(12) United States Patent
Maass et al.

(10) Patent No.: US 6,171,597 B1
(45) Date of Patent: Jan. 9, 2001

(54) ADENO-ASSOCIATED VIRUS VECTOR FOR BOOSTING IMMUNOGENICITY OF FRESHLY ISOLATED TUMOR CELLS

(75) Inventors: Gerhard Maass, Sindelsdorf; Michael Hallek, Schondorf; Christoph Bogedain, Munich, all of (DE)

(73) Assignee: Medigene AG, Martinsried (DE)

( * ) Notice: Under 35 U.S.C. 154(b), the term of this patent shall be extended for 0 days.

(21) Appl. No.: 09/142,443

(22) PCT Filed: Mar. 6, 1997

(86) PCT No.: PCT/DE97/00445

§ 371 Date: May 5, 1999

§ 102(e) Date: May 5, 1999

(87) PCT Pub. No.: WO97/32988

PCT Pub. Date: Sep. 12, 1999

(30) Foreign Application Priority Data

Mar. 6, 1996 (DE) .............................................. 196 08 751

(51) Int. Cl.[7] .......................... A61K 39/23; A61K 39/12; C12N 7/00; C12N 15/00
(52) U.S. Cl. .................................... 424/233.1; 424/199.1; 424/204.1; 435/235.1; 435/320.1
(58) Field of Search ............................. 424/204.1, 199.1, 424/233.1; 435/235.1, 320.1

(56) References Cited

FOREIGN PATENT DOCUMENTS

| WO 94/21808 | 9/1994 | (WO) . |
| WO94/24267A | * 10/1994 | (WO) . |
| WO 95/14101 | 5/1995 | (WO) . |
| WO 95/14771 | 6/1995 | (WO) . |
| WO 95/27494 | 10/1995 | (WO) . |

OTHER PUBLICATIONS

Chiorini et al. 1995, Human Gene Therapy, vol. 6, pp. 1531–1541, Dec. 1995.*

Hallek, M. et al., "Human Lymphoid Tumor Cells Transduced With Recombinant Adeno–Associated Virus (Aav) Vectors Containing B7–1 And B7–2 Genes Provides Potent Costimulatory Signal For T–Cell Proliferation", *Blood* 86(10): (Supp1)1995.

Shaughnessy et al., "Parvoviral Vectors For The Gene Therapy Of Cancer", *Seminars in Oncology*, 23:(1):159–171 (1996).

Wendtner, C.M. et al., "Human Lymphoma Cells Transduced With Recombinant Adeno–Associated Virus (AAV) Vectors Containing B7–1 and B7–2 Genes Provide Potent Costimulatory Signal For T–cell Proliferation", *Oncology* 18: (Supp2) 32 (1995).

Wendtner, C.M. et al., Efficient, Stable And Functional Expression Of Costimulatory Molecules Of B7–1 (CD80) And B7–2 (CD86) in Human Lymphoma Cells By An Improved Adeno–Associated Virus (AAV) Vector, *Journal of Molecular Medicine* 73(4): B13–B14 (1995).

Zhang et al., "Gene Therapy With An Adeno–Associated Virus Carrying An Interferon Gene Results In Tumor Growth Suppression And Regression", *Cancer Gene Therapy* 3(1):31–38 (1996).

* cited by examiner

*Primary Examiner*—Ali Salimi
(74) *Attorney, Agent, or Firm*—Albert P. Halluin; J. David Smith; Howrey Simon Arnold & White, LLP

(57) ABSTRACT

The present invention provides an AAV vector having a foreign DNA coding for a protein that boosts immunogenicity of cells. The invention also provides a vaccine containing such a vector and the use of both.

10 Claims, No Drawings

ADENO-ASSOCIATED VIRUS VECTOR FOR BOOSTING IMMUNOGENICITY OF FRESHLY ISOLATED TUMOR CELLS

This application is the National Stage of International Application No. PCT/DE97/00445, filed Mar. 6, 1997.

FIELD OF THE INVENTION

The present invention relates to an adeno-associated virus vector suited to increase the immunogenicity of cells, a vaccine containing such a vector and the use of both.

BACKGROUND OF THE INVENTION

It is known that in about 0.5% of cancer patients, e.g., those suffering from malignant melanomas, the tumor reverses completely. In many cancer patients, a control of the tumor also takes place, so that it remains in a stable condition over years. This may be because the immune system influences the course of the cancer.

Many attempts have been made to activate the immune system, and to detect and eliminate tumor cells. However, these attempts have not yet yielded satisfactory results.

It is an object of the present invention to provide a product by which the immune system can be stimulated with respect to tumor cells.

Adeno-associated viruses (AAVs) are single-stranded DNA viruses belonging to the Parvovirus family. AAVs require helper viruses, particularly adenoviruses or herpesviruses, for their replication. In the absence of helper viruses AAVs integrate into the host cell genome, particularly at a specific site on chromosome 19.

The genome of AAVs is linear and has a length of about 4680 nucleotides. It comprises two reading frames which code for a structural gene and a non-structural gene. The structural gene is referred to as cap gene. It is controlled by the P40 promoter and codes for three capsid proteins. The non-structural gene is referred to as rep gene and codes for the rep proteins, Rep 78, Rep 68, Rep 52 and Rep 40. The two former proteins are expressed under the control of the P5 promoter while the expression of Rep 52 and Rep 40 is controlled by the P19 promoter. The functions of the Rep proteins are determined inter alia by the control of replication and transcription of the AAV genome.

BRIEF SUMMARY OF THE INVENTION

The present invention relates to an adeno-associated virus vector having a foreign DNA which codes for a protein increasing the immunogenicity of cells.

The present invention is based upon the finding that adeno-associated viruses (AAVS) are suited to transduce tumor cells.

DETAILED DESCRIPTION OF THE INVENTION

An AAV vector according to the invention contains a foreign DNA which codes for a protein boosting the immunogenicity of cells.

The term "AAV vector" refers to any AAV, i.e., virus particle, and the DNA thereof. The AAV vector may be present in wild-type or modified form. The latter also means that it comprises expressible E4 sequences, particularly the ORF6 of the E4 sequences, of adenovirus. Moreover, it may be a system of several components that provide individual or all functions of AAV and/or its DNA. Such a system comprises, e.g., a rep-negative AAV vector and means providing an AAV Rep protein. The AAV vector may be inserted in cells where it integrates into the genome or remains in episomal form.

The term "foreign DNA coding for a protein boosting the immunogenicity of cells" encompasses any foreign DNA that may be integrated within an AAV vector and whose expression product can boost the immunogenicity of cells. Examples of a foreign DNA are genes whose expression products are lacking from or are down-regulated in tumor cells, e.g., MHC-I genes, genes coding for costimulatory molecules, e.g., B7 genes, such as B7.1 and B7.2 genes, genes coding for secretory immunostimulators, e.g., cytokine genes such as IL-2, interferon and GM-CSF genes, and genes that code for tumor-associated antigens, e.g., MAGE1, tyrosinases or viral proteins, e.g., E7 protein of human papilloma virus and EBNA3 protein of Epstein-Barr virus. It is preferred that the expression of the foreign DNA to be controlled by a heterologous constitutive or inducible promoter such as a tissue-specific or tumor-specific promoter. Furthermore, the foreign DNA can be inserted at any position in the AAV vector. In this connection, in some embodiments, the foreign DNA is present in or is present in place of the rep gene. In addition, in some embodiments, several foreign DNAs are present in an AAV vector.

Conventional methods may be used to prepare an AAV vector according to the present invention. For example, an AAV vector can be prepared as a virus particle as follows: Two plasmids are provided wherein the first plasmid is an AAV plasmid that contains a foreign DNA, e.g. a gene for a B7 molecule, between the 5'- and 3'-ITR sequences of AAV. However, this plasmid referred to as pAAV-B7 does not code for the AAV Rep and AAV Cap proteins. These proteins are encoded by a second plasmid. The second plasmid contains an SV40 origin of replication. The second plasmid is referred to as pSV40oriAAV. Both plasmids are transfected into cells expressing an SV40 T antigen. Such cells are, e.g., COS cells. The SV40 origin of replication of pSV40oriAAV is activated by the T antigen, and the plasmid is replicated. A high expression of the AAV Rep and AAV Cap proteins is obtained. AAV vectors are obtained as virus particles by infection of the COS cells with a helper virus, e.g., adenovirus. The titer is between $10^6$–$10^9$ virus-particle/ml.

The immunogenicity of cells can be increased by means of such an AAV vector. In some preferred embodiments, an AAV vector coding for several proteins boosting the immunogenicity of cells is provided. In some other preferred embodiments, several AAV vectors coding for differing proteins boosting the immunogenicity of cells are provided. The increase in immunogenicity can be achieved with cells of any kind, particularly tumor cells or pre-tumor cells such as HPV-transduced cervical cells.

The cells can be transduced with the AAV vector by conventional methods. If the AAV vector is present as a virus particle, the cells may be infected with the viral particle. However, if the AVV vector is present as DNA, it is advisable to transfect the cells therewith. For example, electroporation and lipofection may be used as transfection techniques. The cells can be present in an organism, or the cells to be transduced can also be isolated from an organism, be transduced outside the organism and be introduced into the organism again. Such cells are referred to as autologous cells. Moreover, allogenic cells may be used for the transduction. In this connection, it is favorable for the allogenic cells to belong to a HLA type corresponding to the organism. The person skilled in the art readily understands methods of providing cells with a certain HLA type. In addition, it is preferred for the cells, particularly tumor cells or pre-tumor cells, to be inactivated before introducing them again into the organism. Conventional methods such as irradiation may be used for this purpose.

Cells that are transduced outside an organism may also be co-cultivated with autologous and/or allogenic nuclear blood cells, particularly lymphocytes, based on the organism. The nuclear blood cells may be stimulated by this, and they may be introduced into the organism as such or together with the transduced cells.

The present invention also relates to a vaccine that comprises an AAV vector according to the invention. The vaccine may further comprise conventional auxiliary agents such as buffers, diluents, carriers, etc. In some embodiments, the AAV vector codes for several proteins boosting the immunogenicity of cells. In some other embodiments several AAV vectors are provided that code for differing proteins boosting the immunogenicity of cells. In some preferred embodiments, the vaccine comprises further substances boosting the immunogenicity of cells, particularly tumor-specific antigens. These antigens may be present, e.g., in the form of peptides, particularly synthetic peptides. The antigens may also be present in the form of expression plasmids encoding them that can also code for HLA molecules. It is especially favorable for the vaccine to also contain the cells transduced by the AAV vector and/or the nuclear blood cells stimulated by these cells. In particular, it is preferred that the cells be inactivated. Moreover, it is preferred that the vaccine contain a replication-defective adenovirus whose E4 sequences are operational. Expressible E4 sequences may also be present on a vector or an E4 protein. It is preferred that the vaccine contain a substance supporting DNA replication. This may be. e.g., hydroxy urea, a topoisomerase inhibitor or a DNA synthesis inhibitor in a minor amount. It may also be favorable to irradiate the vaccine, e.g., X-ray or gamma irradiation.

The present invention provides methods to transduce cells, particularly tumor cells or pre-tumor cells, more particularly freshly isolated tumor cells, with great efficiency. A transduction efficiency of 85 to 95% may be obtained. Therefore, the most differing cells of a tumor may be transduced so that the entire antigen profile of the tumor is detected and clonal selection is prevented. Moreover, transduction of the individual cells may be achieved with a small number of AAV vector molecules such as 10 to 20 molecules per cell. Therefore, the transduction does not cause a cytopathic effect. Hence, the immune system recognizes the transduced cells and farther cells having an equal antigen profile and can eliminate them.

Thus, the present invention is suited to boost the immunogenicity of cells, particularly tumor cells or pre-tumor cells. As a result, the present invention is adaptable for use in vivo and/or ex vivo gene therapy of serious diseases such as cancers, including malignant melanoma and cervical carcinoma.

The invention is further explained by the following examples. These examples are provided only to further illustrate the present invention.

EXAMPLE 1

Preparation of an AAV Vector $2\times10^8$ COS cells were added to 2.5 ml RPMI, in each case with 800 $\mu$g of a 1:1 mixture of pSV40oriAAV and pAAV-B7 (cf. description above), and incubated in ice for 10 min. before electroporation was carried out in a total volume of 0.5 ml. Thereafter, the cells were held on ice for 10 min. before they were placed in tissue culture plates. The medium was changed after 24 h and, after another 24 h, the cells were incubated with adenoviruses (10 infectious adenoviruses/COS cell) for 1 h. After another 72 h, the cells were collected and pelleted. The cell pellet was resuspended and homogenized. The homogenizate was adjusted with CsCl to a density of 1.4 g/cm$^3$ and centrifuged at 38,000 rpm for 24 h. Fractions were taken and those having an index of 1.375–1.371 were pooled, centrifuged and dialyzed against Tris buffer. The titer of the AAV virus particles was determined.

EXAMPLE 2

Transduction of Tumor Cells With an AAV Vector

Primary melanoma tissue was isolated from human skin metastases. The melanoma tissue was incubated in a 2% antibiotic solution (antibiotic/antimycotic agent) for 2×30 min. before it was cut into small fragments. The fragments were passed through a metal screens and the resulting cell suspension was pipetted through a fine screen into a centrifuge tube. Erythrocytes and dead cells were removed via a Ficoll gradient before the living melanoma cells were washed 2× with PBS. The melanoma cells were then incorporated into a suitable medium (RPMI 1640, 1% glutamine, 10–20% fetal calf serum, 1% penicillin streptavidin) and placed in tissue culture plates. Prior to the transduction, the melanoma cells were characterized by means of antibodies (S100, HNB-45, company of DA-KO).

$3\times10^5$ melanoma cells were placed in a 24-well tissue culture plate. $3\times10^6$ AAV virus particles of Example 1, which code for a B7 molecule, were placed in 250 $\mu$l serum-free medium on the melanoma cells. After an incubation period of 1 h, 1.5 ml serum-containing medium were added, and the cells were incubated in an incubator.

A FACS analysis of the B7 transduction was carried out. Mouse-anti-human B7.2 monoclonal antibodies (Pharmingen) were placed on the cells which were then bound with a FITC-conjugated goat-anti-mouse antibody. Non-specific bonds were ruled out by isotypic controls. A minimum of 10,000 living melanoma cells was used for each analysis. The percentage of positive cells was defined as fraction which are beyond the 99% range of the control group.

A B7 transduction efficiency of 85–90% was obtained. Parallel experiments in which an AAV virus particle that coded for several proteins boosting the immunogenicity of cells and in which several AAV virus particles that coded for differing proteins boosting the immunogenicity of cells, respectively, was used for the transduction of the tumor cells, showed equal transduction efficiencies for the individual proteins.

EXAMPLE 3

Stimulation of the Immunogenicity of Cells by an AAV Vector (a) The stimulation of the immunogenicity of cells was determined by means of inducing a cytotoxic T cell response.

Melanoma material was removed from various tumor patients. At the same time, blood was taken, and the T cells were accumulated. As described above, the tumor cells were isolated and transduced with the AAV virus particles of Example 1. Thereafter, the T cells were stimulated with the transduced tumor cells. Non-transduced tumor cells were used for the stimulation of the T cells as control.

The results demonstrated that the activity of the cytotoxic T cells can markedly be increased by stimulation with an AAV virus particle according to the invention.

In another experiment, a primary tumor was removed from a tumor patient and treated as described in Example 2. $1\times10^6$ tumor cells were seeded and infected with a multiplicity of infection of 10 after previous gamma irradiation by 30 Gy with B7.1-AAV and GM-CSF-AAV. Four days after the infection, the expression rate of the foreign genes was determined for B7.1 and GM-CSF by means of Facs-Flow and ELISA, respectively. 20 ml of peripheral blood was withdrawn from the patient. Peripheral blood lymphocytes were isolated by density gradient centrifugation using Ficoll Histopaque. $1\times10^7$ lymphocytes were co-cultivated in RPMI1640 medium, containing 10% heat-inactivated human serum, 2 mM glutamine, non-essential amino acids, 2 mM sodium pyruvate and 100 $\mu$g/ml gentamycin or kanamycin, with the AAV-infected tumor cells to stimulate a tumor-specific immune response by cytotoxic T cells. After one week of co-cultivation, 20 U/ml recombinant human interleukin-2 was added to the medium. At intervals of 10 days, further tumor cells infected with the AAV vectors were added to the culture in a ratio of 1:10 to the lymphocytes. After three weeks of cultivation, the lymphocytes were checked in a cytotoxicity test (chromium release test or europium release test) for their capability of lyzing the tumor cells. $1\times10^7$ lymphocytes were reinfused intravenously into the patient.

(b) C57/B16 mice were infected with 5,000 living B16-F10 tumor cells each (mouse melanoma model) into the caudal vein. These tumor cells led to the formation of metastases that could be detected after about 20 days by obduction predominantly in the liver and lungs. On days 3, 10 and 17 following the tumor cell injection, part of the mice were immunized with 300,000 B16-F10 tumor cells that had previously been transduced with an AAV virus particle coding for a B7 protein. Thus, the molecule B7 was found on the surface of the tumor cells.

It showed that the formation of metastases can be inhibited by immunization with an AAV virus particle according to the invention. Parallel experiments in which an AAV virus particle which coded for several proteins boosting the immunogenicity of cells and in which several AAV virus particles that coded for differing proteins boosting the immunogenicity of cells, respectively, was used for the transduction of the tumor cells, showed an even more intense inhibition of the formation of metastases.

(c) C57/B16 mice were injected subcutaneously in each case 100,000 B16-F10 tumor cells into the back. This resulted in the formation of a tumor that had a circumference of 0.3–0.5 cm after 10 days. At that time, the AAV virus particle of Example 1 ($10^6$–$10^8$ particles) was injected directly into the tumor.

The results demonstrate that after the transduction with an AAV virus particle according to the invention, the tumor cells are detected by the immune system and the tumor is eliminated.

What is claimed is:

1. A method for boosting the immunogenicity of freshly isolated tumor cells comprising the step of transducing said tumor cells with an Adeno-Associated Virus (AAV) vector comprising a foreign DNA coding for a protein that boosts the immunogenicity of a cell.

2. The method according to claim 1, wherein the foreign DNA comprises a gene selected from the group consisting of a gene whose expression product is lacking or is down-regulated in said tumor cells, a gene coding for a co-stimulatory molecule, a gene coding for a secretory immunostimulator, and a gene coding for a tumor-associated antigen and a viral protein.

3. The method according to claim 1, wherein the AAV vector comprises more than one foreign DNAs.

4. The method according to claim 1, wherein the foreign DNA is controlled by a heterologous constitutive or inducible promoter.

5. The method according to claim 4, wherein the promoter is a tissue-specific or tumor-specific promoter.

6. The method according to claim 1, wherein said AAV vector is in the form of a vaccine which contains conventional auxiliary agents.

7. The method according to claim 6, wherein the vaccine comprises more than one AAV vector and each AAV vector codes for a different protein that boosts the immunogenicity of a cell.

8. The method according to claim 6, wherein the vaccine further comprises substances that boost the immunogenicity of a cell.

9. The method according to claim 8, wherein the substances are tumor-specific antigens.

10. The method according to claim 6, wherein the AAV vector is present in freshly isolated tumor cells.

* * * * *